United States Patent [19]

Newman et al.

[11] 4,204,550

[45] May 27, 1980

[54] APPARATUS FOR FRACTIONATION OF A STANDARD PUFF OF SMOKE FROM A SMOKING MACHINE

[75] Inventors: Richard H. Newman, Richmond; William L. Jones, Jr., Mechanicsville; Robert W. Jenkins, Jr., Richmond, all of Va.

[73] Assignee: Philip Morris Incorporated, New York, N.Y.

[21] Appl. No.: 17,989

[22] Filed: Mar. 7, 1979

[51] Int. Cl.² ............................................. A24F 13/00
[52] U.S. Cl. .................................... 131/171 R; 73/28; 55/270; 55/274; 131/10.3
[58] Field of Search ............. 131/171 R, 10.3; 73/28; 55/270, 274

[56] References Cited

U.S. PATENT DOCUMENTS

| 3,376,874 | 4/1968 | Kim et al. | 131/10.3 X |
| 3,433,054 | 3/1969 | Mutter | 131/71 R X |
| 3,460,374 | 8/1969 | Parks | 73/28 |

*Primary Examiner*—Stephen C. Pellegrino
*Attorney, Agent, or Firm*—Arthur I. Palmer, Jr.; George E. Inskeep

[57] ABSTRACT

A holder for a flat circular filter attached to a smoking machine is provided with a rotatable support for the filter pad. The smoke inlet and suction outlet for the filter holder are offset from the center of the pad and holder and are in matching positions at opposite faces of the pad. At the initiation of each puff, a rotator is synchronized to turn the support and pad through a predetermined arc so that the smoke particulates are spread along said arc of the filter pad. The products of an individual puff are thus positioned for the study of puff fractions. Multiple puffs may be handled on one pad.

5 Claims, 5 Drawing Figures

APPARATUS FOR FRACTIONATION OF A STANDARD PUFF OF SMOKE FROM A SMOKING MACHINE

BACKGROUND ART

Automated smoking machines have been in use for many years. The filter for particulates, which is commonly used in such machines, is known as a Cambridge filter (Cambridge Filter Corporation, Syracuse, N.Y.) and is well known for its high efficiency of particulates removal (specified as greater than 99.9 percent for particles larger than 0.3 micron at standard smoking machine conditions). This filter consists of a flat circular pad of glass fibers clamped in a holder of the type illustrated and described, for example, in U.S. Pat. No. 3,433,054 (see FIGS. 1 and 2, Parts 50 and 62).

Mutter, in the above-mentioned patent, discloses apparatus that has the purpose of segregating the particulates from the first puffs, the second puffs, and so on from a set of cigarets. The machine enables an investigator to weigh or analyze the particulates from various puffs in order to note variations as smoking progresses.

DISCLOSURE OF INVENTION

It is desirable at times to examine the particulates to determine how they vary within a puff as well as from one puff to the next. The present invention makes this possible by rotating the filter to spread the particulates.

BEST MODE FOR CARRYING OUT THE INVENTION

Figure 1:
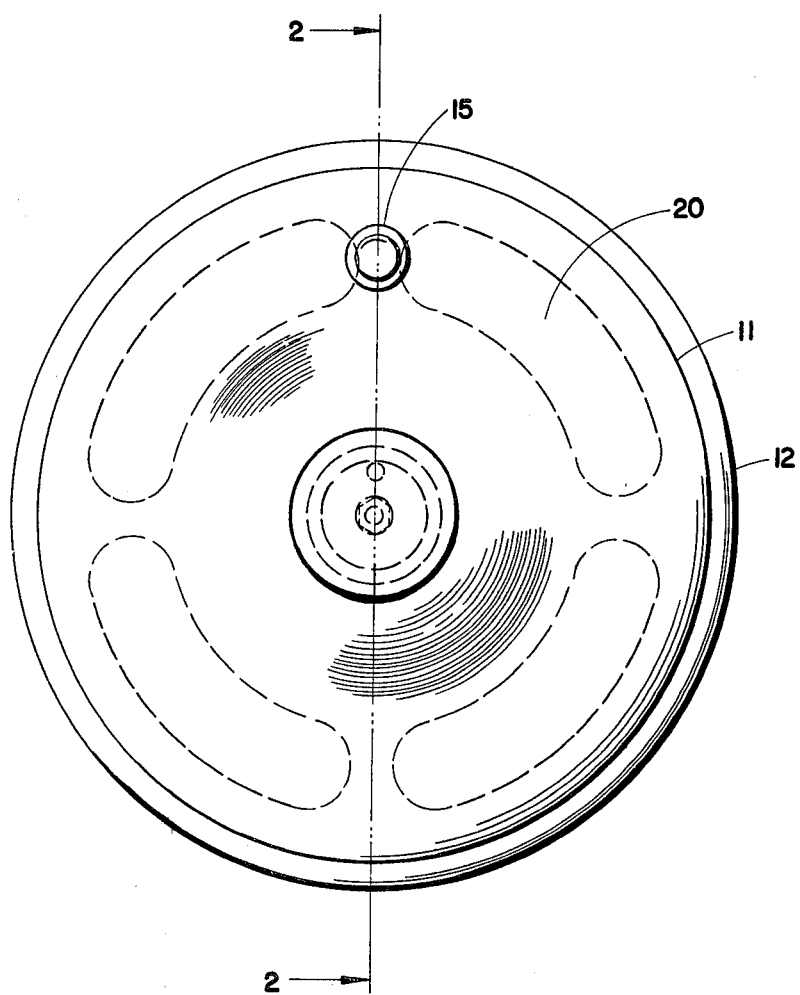
FIG. 1 is a plan view of the filter and holder of the invention.

The filter/filter holder of the invention is intended to replace the conventional filter and holder of a smoking machine, as for example Part 114 of FIG. 1 in U.S. Pat. No. 3,460,374. Its purpose is to distribute the particulates from each puff as an arcuate band on the filter disc so that one end of each stripe will represent the beginning of the puff and the other end the finish. In this way the particulates from the puff can be studied sequentially or divided into several fractions for analysis according to the position in the puff. For example, if radioactive or stable isotopes are incorporated as part of an additive to the tobacco rod in a test cigarette, fractional analysis of the stripe representing a puff will show at what point in the puff the additive or its decomposition products were eluted.

Figure 2:
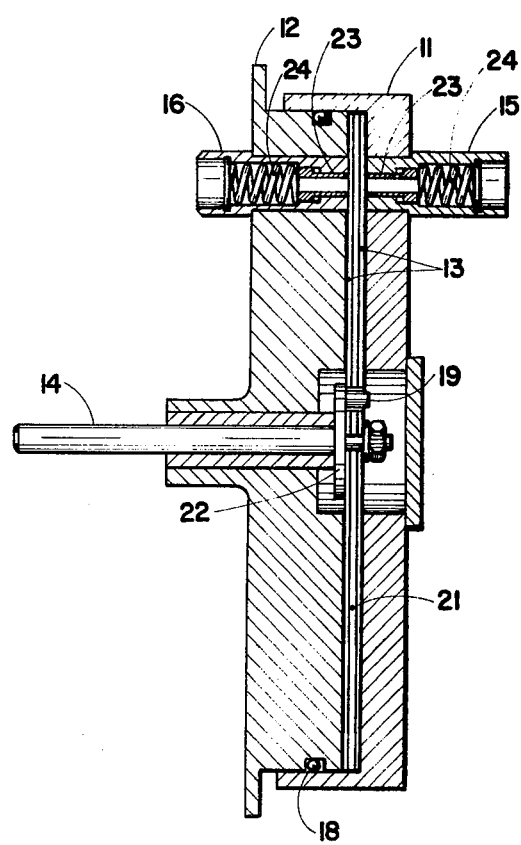
FIG. 2 is a sectional view of the filter and holder taken along the line 2—2 of FIG. 1.

Referring now to FIGS. 1 and 2, a disc of Cambridge filter material 21 centered on a support pad 13 is seated on the male portion 12 of the filter holder. The second support pad 13 is positioned on top of the filter disc with its openings 20 matching those in the first pad. The positioning of the two pads in register with each other is made easy by the opening already present in each to accept the roller pin 19 protruding from hub 22 attached to the rotator shaft 14. The disc 21 has had a central hole and a second hole punched to accommodate the extension of shaft 14 and the pin 19. A nut and washer are then put on this shaft extension to secure the assembly. The two support pads 13 are of a low-friction material, such as polytetrafluoroethylene resin, so that the assembly can rotate easily between the two portions of the filter holder 11 and 12. The female portion 11 is then fitted over the male portion 12, which is already supplied with O-ring 18 for sealing. The cigarette mouthpiece 15 must be positioned reasonably closely in register with the suction port 16 of the other portion of the holder. Ports 15 and 16 are desirably fitted with sleeves 23 of low-friction material such as polytetrafluoroethylene; these sleeves are urged against the filter disc 21 during the puffing cycle, so as to confine the smoke stream, by the springs 24 secured by lock washers; at the end of the puff the sleeves are forced outward by the intervening support pads.

The shaft 14 is then rotated, if necessary, so that strips separating the open arcs of the support pads are aligned with the cigarette mouthpiece and suction port, as shown in FIG. 1. This is the starting position for a smoking cycle. At this position the sleeves 23 are in contact with the separating strips.

The male portion of the holder 12 may be fabricated from steel, aluminum, or the like. The female portion 11 may also be made of like material, but preferably is of a transparent material, such as glass or poly(methyl methacrylate) plastic; the male portion could also be made from such material. The transparency facilitates the positioning of the holder parts and the rotating element and permits observation during the smoking operation.

Figure 3:
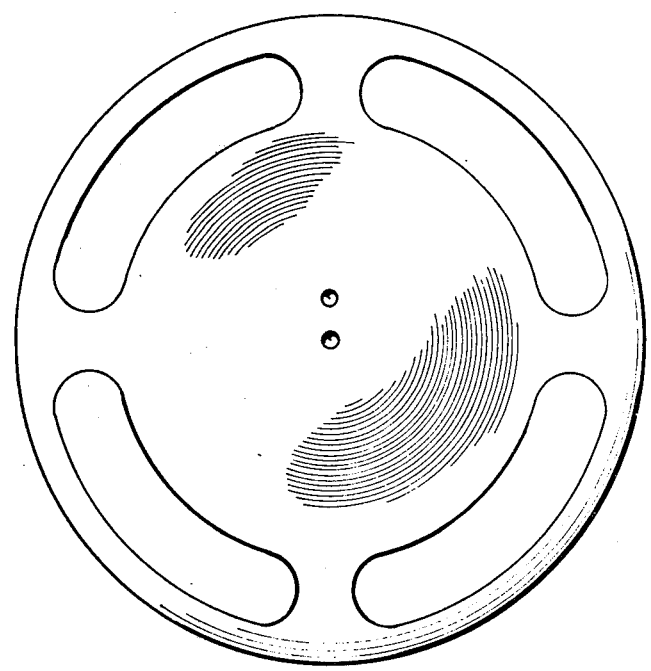
FIGS. 3 and 4 illustrate alternative designs for the support pads to hold the filter disc.
Figure 4:
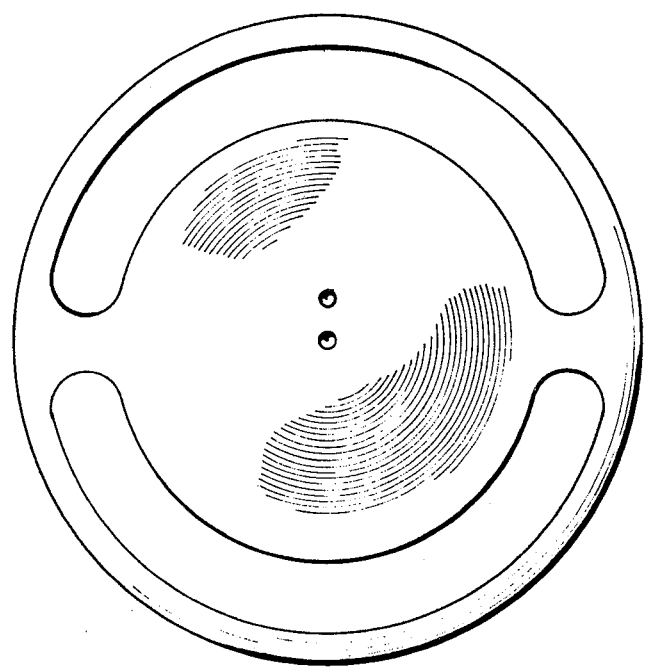

The support pads for the filter disc are made as mirror-image duplicates and, because of symmetry, are normally interchangeable. FIGS. 3 and 4 illustrate pads having 90 and 180 degree arc openings respectively, providing for 4- or 2-puff samples.

In operation, the shaft 14 is driven, directly or indirectly, by a variable-speed motor controlled by a switch synchronized with the smoking machine puff cycle. The speed of rotation is adjusted so that during a single puff (conventionally 2 seconds) the disc will be rotated through the arc spanned by one opening in the support pads, e.g., 90 degrees in FIG. 3. The smoking machine simultaneously applies suction to suction port 16 and thus through the filter disc to mouthpiece 15 into which has been inserted a lighted cigarette. The puff is thus distributed uniformly along the length of the opening. An example of circuitry providing for this synchrony is shown in FIG. 5.

Figure 5:
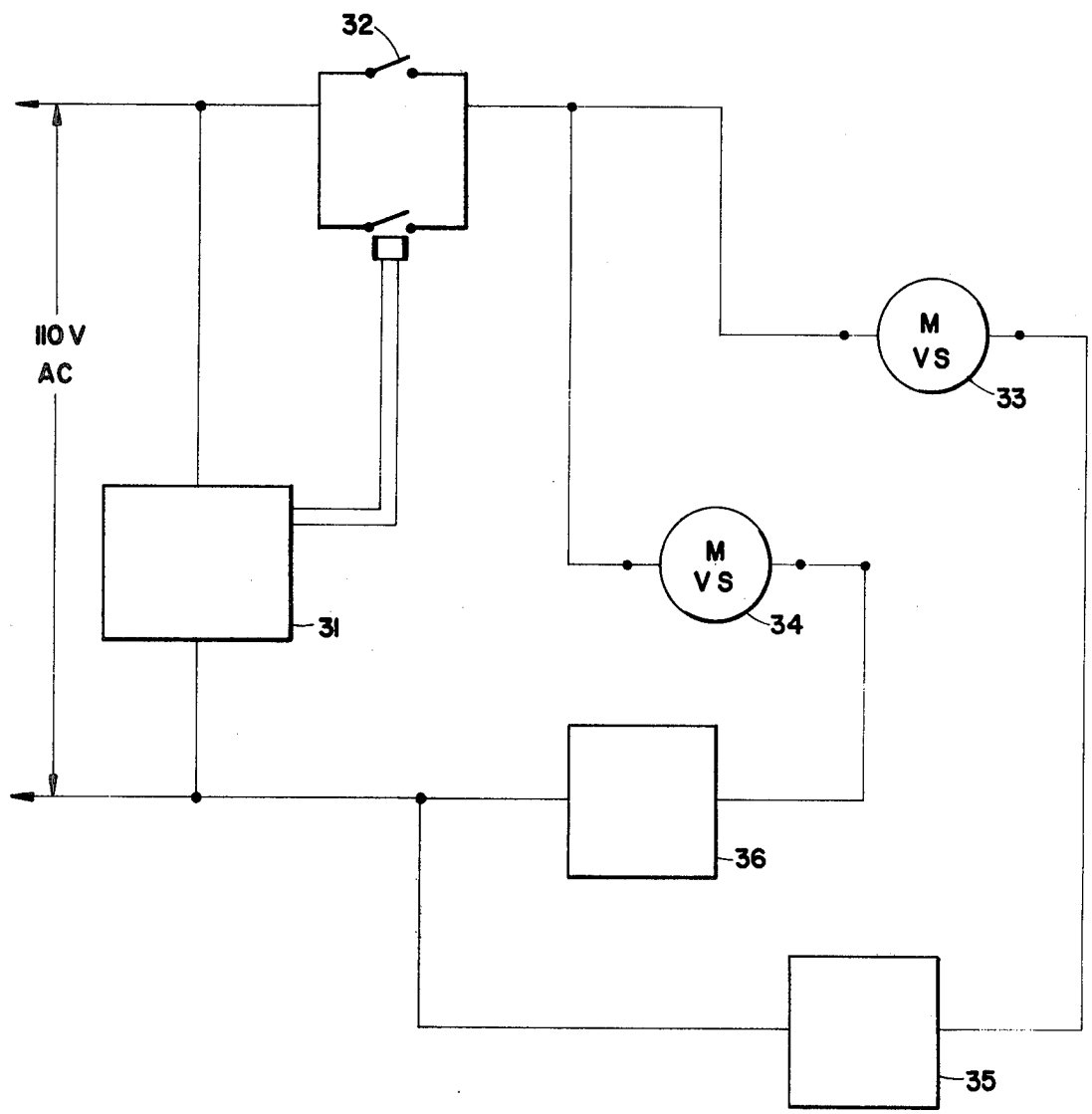
FIG. 5 is a schematic showing of the electric circuitry for controlling a smoking machine and the motor for rotating the filter.

In FIG. 5, the timer/relay 31 is set for the desired smoking machine cycle, for example 2-second activation every 60 seconds. The two variable-speed motors 33 and 34, the first operating the puffing mechanism of the smoking machine, the second causing the rotation of shaft 14 of the filter holder (FIG. 1) are provided with speed controls. The manual speed control 35 for motor 33 is adjusted in usual fashion to insure one puffing cycle of the machine during the 2-second activation cycle; the speed control 36 for motor 34 is adjusted as described above for filter holder rotation. Manual switch 32 permits operation of the motors independently of the timer 31, in special situations such as preliminary observation of mechanical operations.

The following example gives details of an application of the apparatus of the invention.

EXAMPLE

A filter holder, as shown in FIGS. 1 and 2, with filter area being 6 inches in diameter, was attached to a smoking machine like that of Parks in U.S. Pat. No. 3,460,374 and fitted with a disc of Cambridge filter material held between "Teflon" supports as shown in FIG. 3. The machine was adjusted to draw one 2-second puff of 35 cc every 60 seconds, and the variable-speed motor driving the shaft of the filter holder was actuated by the same switch for 2 seconds and adjusted to rotate 90 degrees during that time.

Cigarettes were doped uniformly with $^{14}$C-dotriacontane by applying it at 3.91 mCi/mm in hexane. These were conventional 67 mm non-filter cigarettes. Five such cigarettes were smoked. The first four puffs from each after the lighting puff were collected on the machine, and the filter discs were carefully sectioned. The filter strips carrying the particulates from each puff were divided into four equal parts and the radioactivity determined on each as well as on the ash and the butt (including filter). The radioactivity findings are tabulated in Table 1 as percentages of the total applied.

Table 1

| PUFF FRACTION VERSUS ACTIVITY | | |
|---|---|---|
| Puff | Section | Percent Activity |
| 1 | a | 0.8 |
|   | b | 0.9 |
|   | c | 0.9 |
|   | d | 0.6 |
| 2 | a | 0.6 |
|   | b | 0.9 |
|   | c | 0.8 |
|   | d | 0.6 |
| 3 | a | 0.8 |
|   | b | 1.3 |
|   | c | 1.5 |
|   | d | 1.0 |
| 4 | a | 0.5 |
|   | b | 0.9 |
|   | c | 1.1 |
|   | d | 0.8 |
|   | Ash | 0.01 |
|   | Butt | 85.86 |
|   | TOTAL | 99.87 |

In certain situations, a combustible filter material might be required in place of the Cambridge material to make possible an ashing or like analytical approach. Low-ash filter paper could then be employed in sufficient thickness to retain a desired proportion of smoke particulates.

What is claimed is:

1. For use with an automatic smoking machine for testsmoking cigarettes or the like, a filter holder and support comprising:
    (a) a male filter holder portion having a flat circular surface,
    (b) a female filter holder portion having a flat circular surface and a peripheral wall capable of fitting removably over said male portion,
    (c) a rotatable shaft and hub fitted by means of a bushing in a central opening in one of said holder portions,
    (d) a tubular suction port attached to one of said filter holder portions at an opening distinct from said central opening and positioned in its flat surface at a distance from the circular center,
    (e) a tubular cigaret mouthpiece attached to the other of said filter holder portions at an opening distinct from said central opening and at a distance from the circular center equal to that of the suction port, and
    (f) two filter support pads of flat circular configuration, each having at least one arcuate opening at a distance from the center equal to that of the suction port, and being removably attached to said rotatable shaft and hub.

2. The filter holder and support of claim 1 having a drive means for rotating the said shaft and hub at controlled time intervals.

3. The filter holder and support of claim 2 provided with a control system capable of synchronizing the rotation of the shaft and hub with the operation of the smoking machine.

4. The filter holder and support of claim 2 having an adjustable speed control for the said drive means.

5. The filter holder and support of claim 1 wherein the said female filter holder portion is constructed primarily of transparent material.

* * * * *